United States Patent
Courtney (10) Patent No.: US 10,307,762 B2
(45) Date of Patent: Jun. 4, 2019

(54) THERMAL CYCLER HAVING A TEMPERATURE ANALYSIS AND/OR VERIFICATION UNIT AND A METHOD FOR ANALYZING OR VERIFYING A THERMAL PERFORMANCE OF A THERMAL CYCLER AND FOR CALIBRATING THE THERMAL CYCLER

(71) Applicant: Hain Lifescience GmbH, Nehren (DE)

(72) Inventor: James Courtney, Kent (GB)

(73) Assignee: Hahn Lifescience GmbH, Nehren (DE)

( * ) Notice: Subject to any disclaimer, the term of this patent is extended or adjusted under 35 U.S.C. 154(b) by 190 days.

(21) Appl. No.: 15/103,543

(22) PCT Filed: Dec. 2, 2014

(86) PCT No.: PCT/EP2014/076158
§ 371 (c)(1),
(2) Date: Jun. 10, 2016

(87) PCT Pub. No.: WO2015/086365
PCT Pub. Date: Jun. 18, 2015

(65) Prior Publication Data
US 2016/0361719 A1    Dec. 15, 2016

(30) Foreign Application Priority Data

Dec. 12, 2013 (EP) .................................. 13196781

(51) Int. Cl.
*B01L 7/00* (2006.01)
*B01L 3/00* (2006.01)
*C12P 19/34* (2006.01)

(52) U.S. Cl.
CPC ............ *B01L 7/52* (2013.01); *B01L 3/50851* (2013.01); *C12P 19/34* (2013.01); *B01L 2200/028* (2013.01); *B01L 2200/147* (2013.01); *B01L 2200/148* (2013.01); *B01L 2300/025* (2013.01); *B01L 2300/041* (2013.01); *B01L 2300/0663* (2013.01); *B01L 2300/0829* (2013.01); *B01L 2300/1805* (2013.01); *B01L 2300/1822* (2013.01); *B01L 2300/1894* (2013.01)

(58) Field of Classification Search
None
See application file for complete search history.

(56) References Cited

U.S. PATENT DOCUMENTS

| 2009/0220984 A1 | 9/2009 | Dinges |
| 2010/0150203 A1 | 6/2010 | Timmann et al. |
| 2012/0003726 A1 | 1/2012 | Jones et al. |
| 2012/0039354 A1* | 2/2012 | Dilly ................... B01L 3/50851 374/141 |
| 2013/0078733 A1 | 3/2013 | Holmes et al. |
| 2014/0255945 A1* | 9/2014 | Hendrikx .................. B01L 7/52 435/6.12 |

OTHER PUBLICATIONS

International Preliminary Report on Patentability in PCT/EP2014/076158, dated Mar. 1, 2016.
International Search Report and Written Opinion in PCT/EP2014/076156, dated Feb. 4, 2015.

* cited by examiner

*Primary Examiner* — Gary Benzion
*Assistant Examiner* — Olayinka A Oyeyemi
(74) *Attorney, Agent, or Firm* — Curatolo Sidoti Co., LPA; Salvatore A. Sidoti; Joseph G. Curatolo (57) ABSTRACT

Provided is a thermal cycler including a housing, the housing with a thermal block having sample wells, each for receiving a test sample in a sample vessel, an electric heater for heating the thermal block, a power supply and an electronic control for controlling the electric heater, and a temperature analysis and/or verification unit for analyzing and/or verifying a thermal performance of the thermal block. Also provided is a method for analyzing or verifying a thermal performance of a thermal cycler and for calibrating the thermal cycler. The thermal cycler has a temperature analysis and/or verification unit integrated into the housing and connected to the power supply and electronic control by an internal interface, whereas the method is characterized by the following steps: providing the thermal cycler with an integrated temperature analysis and/or verification unit and using the integrated temperature analysis and/or verification unit for self-calibration of the thermal cycler.

4 Claims, 9 Drawing Sheets

THERMAL CYCLER HAVING A TEMPERATURE ANALYSIS AND/OR VERIFICATION UNIT AND A METHOD FOR ANALYZING OR VERIFYING A THERMAL PERFORMANCE OF A THERMAL CYCLER AND FOR CALIBRATING THE THERMAL CYCLER

CROSS REFERENCE TO RELATED APPLICATIONS

This application is a national stage application of International Application No. PCT/EP2014/076158, filed 2 Dec. 2014, which claims priority from European Patent Application No. 13196781.2, filed 12 Dec. 2013, which applications are incorporated herein by reference.

This invention relates to thermal cyclers. Specifically, the present invention is directed to a thermal cycler having a temperature analysis and/or verification unit according to the preamble of claim 1. The present invention is further directed to a method for analyzing or verifying a thermal performance of a thermal cycler and for calibrating the thermal cycler according to the preamble of claim 12. In addition the present invention relates to a use of the thermal cycler and the method according to claim 15.

STATE OF THE ART

A thermal cycler (also known as a thermocycler, PCR machine or DNA amplifier) is a laboratory apparatus most commonly used to amplify segments of DNA via the polymerase chain reaction (PCR), which is now common place within Molecular Biology, in both Research and Diagnostics sectors. However thermal cyclers may also be used in laboratories to facilitate other temperature-sensitive reactions, including but not limited to restriction enzyme digestion or rapid diagnostics. Thermal cyclers are generally equipped with a thermal block having an array of sample wells or holes where tubes or other vessels holding the test samples can be inserted. Quality thermal cyclers often contain silver blocks to achieve fast temperature changes and uniform temperature throughout the block. After the insertion of the vessels into the sample wells or holes the temperature of the thermal block is raised and lowered in discrete, pre-programmed steps for alternately heating and cooling the test samples during the cycles of the PCR. In case of a poorly performing thermal cycler where the temperature of the thermal block is not uniform or where the thermal block is not heated or cooled according to an exact predetermined target temperature curve there is a potential to, for example, provide false-negative PCR results.

In order to ensure a consistent and accurate thermal performance of thermal cyclers, i.e. thermal uniformity of the thermal block or well-to-well uniformity, temperature accuracy, heating and cooling rates, temperature overshoot and timing, it is necessary to analyze or verify these parameters and eventually to calibrate the thermal cyclers in case of a poor thermal performance.

At present there are three possible alternatives available to the user for analysis or verification of thermal cycler thermal performance:

1. Manufacturer Service Contract

Here the users opt for a service agreement with the actual manufacturer of the thermal cycler. A test engineer from the manufacturer visits the users and performs a verification test on-site.

Although the true cost of this exercise is often difficult to determine, as it is typically included within the purchase price of the thermal cycler, it can be expensive. Costs should be considered on a case-by-case basis.

Typically manufacturers recommend performing this test on an annual basis, a frequency of verification typically not commensurate with most quality control requirements because thermal cycler performance could begin to degrade immediately following any on-site check.

Even though eventually a calibration of the thermal cycler is possible and adjustments can be made to the temperature if required, because the manufacturer's test engineer has intimate knowledge of the manufacturer's thermal cyclers, there are quite a few drawbacks associated with manufacturer service contracts:

When the on-site verification is performed by an external/visiting test engineer the testing must be well organized as all the manufacturer's thermal cyclers on site must be available for verification within a specified period. During this period the thermal cyclers are not available for PCR.

Often on-site verification contracts are only commercially suited for sites which have many thermal cyclers to test as the costs of having an engineer visit to verify only one or few thermal cyclers would typically prove prohibitive.

Maintaining a history record of each thermal cycler is very difficult. Such a history record will typically involve a manual comparison of text-based test reports, where the users themselves have to pick-out out pertinent data and then have to manually enter the data into a spreadsheet-type application for comparison.

2. Verification Using Purchased Test Equipment

In this instance the users purchase a piece of proprietary temperature test equipment and perform the verification testing themselves. Naturally there is a significant financial investment required with this approach, particularly when considering the wide array of test equipment that may require purchasing to ensure compatibility with the various makes and models of thermal cyclers that require testing.

Often the test equipment purchased is identical to that utilized for testing carried out under manufacturer service contracts. However the training required to operate this equipment correctly, in a manner that will achieve accurate, repeatable and meaningful results, is seldom accessible. In addition interpretation of the results is often very subjective. Typical test equipment is designed to be operated by trained personnel—often requiring a specific skill set to obtain satisfactory and valid test results.

Pass fail limits are typically not provided with the test equipment as this causes friction between the manufacturer, the test equipment supplier and the user. How can a user be expected to achieve the same test results as those the manufacturer achieves in a fully controlled environment with their own different, dedicated test equipment.

Furthermore manufacturers are reluctant at best to pass on details of testing procedures, making comparison against published specifications all but impossible. Where pass/fail thermal performance limits are available then they tend to be supplied in the form of wider-tolerance "field limits". These limits naturally lead to confusion as they are different to published specifications in every regard.

The issue of how to perform the test now comes into question; inconsistencies in test protocols, apparatus and methodology are all variables that can skew results.

The selection and purchasing of the correct test equipment is an issue, sometimes the configuration of a "correct test system" can be extremely difficult.

Often the systems available for purchase are particularly complex in operation, having to cater for many different makes and models.

Although this method allows the user to conduct a thermal test on thermal cyclers, in case of a discrepancy their calibration is often not possible. Should calibration be required the discrepancy has to be reported to the manufacturer. The manufacturer then has to confirm the results, a process often causing friction with respect to published specification etc, and then an engineer has to visit the site or the thermal cycler in question has to be returned to the manufacturer for calibration.

Often the user has no alternative other than to simply leave the thermal cycler unadjusted, despite knowing that its thermal performance is poor.

Maintaining a history record of the unit is again very difficult; this typically will involve a manual comparison of text-based test reports, where the users themselves have to pick-out out pertinent data and then have to manually enter the data into a spreadsheet-type application for comparison.

3. Using a Thermal Cycler Servicing Company

Here the users can contract-out the job of thermal cycler verification to a third party thermal cycler servicing company that specializes in thermal cycler temperature verification. As with the manufacturer service contract a test engineer typically visits the customer and performs the verification testing on-site. If the user has many different makes and models of thermal cyclers that require validation this solution does offer cost advantages as it makes little sense for the user to purchase all the different variations of test equipment that are available.

Thermal cycler servicing companies generally offer a more detailed verification of thermal performance compared to that provided as part of a manufacturer's service contract. However the test equipment used is not necessarily well suited to the specific thermal cycler being tested and manufacturers will disregard any test data yielding from a non-approved source.

In addition thermal cycler servicing companies generally utilize the test equipment that is available for purchase by the end user. Therefore the same limitations apply as for the validation using purchased test equipment.

In the unusual event of the servicing company having the technical know-how to recalibrate the thermal cycler it remains that in most instances this process will invalidate any warranty on the instrument.

Maintaining a history record of the unit is again very difficult; this typically will involve a manual comparison of text-based test reports, where the users themselves have to pick-out out pertinent data and then have to manually enter the data into a spreadsheet-type application for comparison.

Therefore none of the methods cited above provide a wholly satisfactory solution for the user.

The external test equipment used in the methods cited above generally is in the form of a temperature analysis and/or verification unit that comprises a temperature probe plate with a plurality of temperature probes and further comprises a separate external control unit that communicates with the temperature probes of the probe plate and is equipped with a power supply, a processor for controlling the temperature analysis and/or verification process as well as a memory and a display for storing or displaying the test results respectively.

DETAILED DESCRIPTION OF THE INVENTION

It is therefore an object of the present invention to provide a thermal cycler and a method for verifying a thermal performance of a thermal cycler and for calibrating the thermal cycler that will avoid or at least ameliorate the above mentioned drawbacks.

In order to achieve these objects the present invention provides a thermal cycler according to claim 1 and a method for verifying a thermal performance of a thermal cycler and for calibrating the thermal cycler according to claim 12. Furthermore the present invention provides the use of such a thermal cycler and/or method for Polymerase Chain Reaction (PCR).

The thermal cycler and method according to the invention provide the following advantages:

Temperature verification: The temperature analysis and/or verification unit does not only provide validation, i.e. that the thermal cycler is operational, but also verification, i.e. that the temperatures achieved in the samples wells are according to specification.

Self Calibration: The results generated by the integrated temperature analysis and/or verification unit can be directly used to verify the thermal performance of thermal cycler and, if necessary, to allow the thermal cycler to automatically calibrate itself.

Frequency of Test: Analyses and/or verification of the thermal performance of the thermal block can be performed as frequently as desired with no additional cost penalties. Annual tests can be replaced with weekly or even daily checks.

Usability: The integrated temperature analysis and/or verification unit is specifically designed for use with the specific thermal cycler and can be easily adapted to different thermal block designs used on the Thermal Cycler. The thermal cycler can have a simple, bespoke design, where no formal training is required for foolproof operation.

The integrated temperature analysis and/or verification unit verification system can be made identical to the temperature analysis and/or verification unit that is used for quality control at the manufacturer which ensures that data is directly comparable. The calibration procedure can be also made identical to the calibration procedure used by the manufacturer for quality control so that the pass/fail limits being similarly identical.

The thermal cycler itself maintains its own history which allows for automatic lifetime monitoring/trend analysis of all key thermal performance values, all results being stored onboard electronically in a memory of the thermal cycler's electronic control or in a memory of the integrated temperature analysis and verification unit. No manual interpretation is required by the user as the results can be electronically retrieved or indicated on a display of the thermal cycler on demand.

The level of thermal validation is fully controllable by the user, ranging from quick "health checks" to a fully in-depth, detailed analysis.

A baseline can be set by the user, either typical PCR-temperatures or temperatures that are of particular interest to the user, and the variation from which can be analyzed when required. This allows the user to instantly spot any deviation in performance away from the norm.

Compared to a manufacturer service contract where a test engineer from the manufacturer performs temperature verification tests on-site there is no need to thoroughly organize the tests as they can be performed whenever need arises and can be independently performed for each thermal cycler so that downtime of a large number of thermal cyclers can be avoided.

Compared to the verification using purchased test equipment an integrated temperature verification and calibration unit will always be customized or tailor-made for the thermal cycler with which it is used. If necessary, the training required to operate the integrated temperature verification in a manner that will achieve accurate, repeatable and meaningful results, will be provided by the manufacturer of the thermal cycler together with the training to operate the thermal cycler itself. Therefore there will be no questions how to perform the test and how to adapt test equipment to a particular thermal cycler. This will generally result in satisfactory and valid test results without any inconsistencies in test protocols.

Compared to the use of a thermal cycler servicing company the test equipment used is perfectly suited to the specific thermal cycler being tested because it has been developed and undergone quality control together with that specific thermal cycler. Due to the fact that the integration of the temperature verification and calibration unit into the thermal cycler will be generally performed during the manufacture of the thermal cycler any test data will yield from a source approved by the manufacturer and calibration will not invalidate any warranty on the instrument.

Probably most important compared is the ability for self-calibration which in not possible in any of the three alternatives presently at hand.

According to a preferred embodiment of the invention the integrated temperature analysis and/or verification unit comprises a temperature probe plate having a plurality of temperature probes for measuring the temperature within selected sample wells. Such temperature probe plates have already proven reliable in exterior test equipment used for the verification of thermal performance of thermal cyclers. Preferably the temperature analysis and/or verification unit comprises a closed loop control for calibration of the electric heater means in dependency of the temperature measured by the temperature probes within selected sample wells.

When not in use, i.e. during normal operation or downtime of the thermal cycler, the temperature probe plate is preferably stowed on the thermal cycler itself and most preferably accommodated within a stowage compartment of the housing from where it can be removed and placed on the thermal block for performing a temperature analysis and/or verification, when required. The opening of the stowage compartment is advantageously located on top of the housing close to the thermal block and the sample wells for easy access to the probe plate, when required.

According to a first alternative the temperature probes are fixed to the temperature probe plate so that they are always associated with specific sample wells. According to a second alternative the temperature probes are variable probes that are interchangeable and can be selectively attached to different sockets of the temperature probe plate so that they can be used to verify or calibrate different sample wells. This is advantageous to tackle specific requirements, for example a detailed thermal gradient analysis or a verification or calibration of a specific area of the sample wells that is giving atypical performance. The latter alternative also provides for non-standard block or well dimensions or for the attachment of leaded probes to the sockets of the temperature probe plate.

According to a further preferred embodiment of the invention all the temperature probes carry their own unique identity which is automatically recognized by software in the thermal performance analysis and/or verification unit. This will ensure integrity of temperature data from one test to the next, regardless of the position of the temperature probe on the probe plate or in one of the sample wells respectively.

Preferably the temperature probe plate is connected to the internal interface by mating electrical contacts or by an electrical plug-in connection when the temperature probe plate is located on the thermal block. The electrical connection can be disconnected for removal of the temperature probe plate from the thermal cycler so that the temperature probe plate can be calibrated upon demand externally and separately from the thermal cycler.

Preferably the thermal cycler has a heated lid that can be closed. In the closed state the heated lid presses against the lids of the reaction or sample vessels and prevents condensation of water that has evaporated from the reaction mixtures or test samples on the insides of the lids.

According to another embodiment of the invention the internal interface of the thermal cycler is connected to the probe plate by means of a cable extending from the stowage compartment so that the probe plate can be kept connected to the thermal cycler when it is within the stowage compartment.

In order to keep the footprint of the thermal cycler as small as possible the stowage compartment preferably has a slot-like form for inserting a narrow side of the probe plate into an opening of the compartment while the temperature probes preferably project from a broad side of the probe plate as with conventional temperature probe plates. In order to avoid damaging the prevent the projecting temperature probes during insertion or removal of the probe plate into/from the stowage compartment the latter preferably comprises guiding means for guiding the probe plate during insertion and removal.

According to another preferred embodiment of the invention the temperature analysis and/or verification unit is connected to a display on the housing by means of the internal interface. In this way the display of the thermal cycler can be used for displaying the test results from the temperature analysis and/or verification unit, all key thermal performance values or trend analysis without the need for an external display. Furthermore the display allows for a visual comparison of the thermal cycler's thermal performance from test to test. Preferably the display is a touch-screen display that can be used to start the temperature analysis and verification process and/or the self-calibration process.

According to a further preferred embodiment of the inventive method the analysis and/or verification unit comprises a temperature probe plate having a plurality of temperature probes for measuring the temperatures within selected sample wells of a thermal block of the thermal cycler and in the further steps of disconnecting an electrical connection between the temperature probe plate and the thermal cycler and removing the temperature probe plate from the thermal cycler for separate external calibration of the temperature probe plate.

According to a further preferred embodiment of the inventive method, the integrated analysis and/or verification unit comprises a temperature probe plate having a plurality of temperature probes for measuring the thermal performance of the thermal block within selected sample wells, wherein the temperature probes communicate temperature values to the electronic control by means of an interface of the thermal cycler and wherein the electronic control compares the temperature values from the temperature probes with target temperature values and initiates a self-calibration process of the thermal cycler when required. Preferably the self-calibration process of the thermal cycler is in the form of a closed-loop process using the temperature values communicated by the temperature probes of the temperature analysis and/or verification unit for modification of the performance of the electric heater means.

The present invention is illustrated by reference to the drawing figures, encompassing different views of two embodiments of the invention, wherein.

Figure 1:
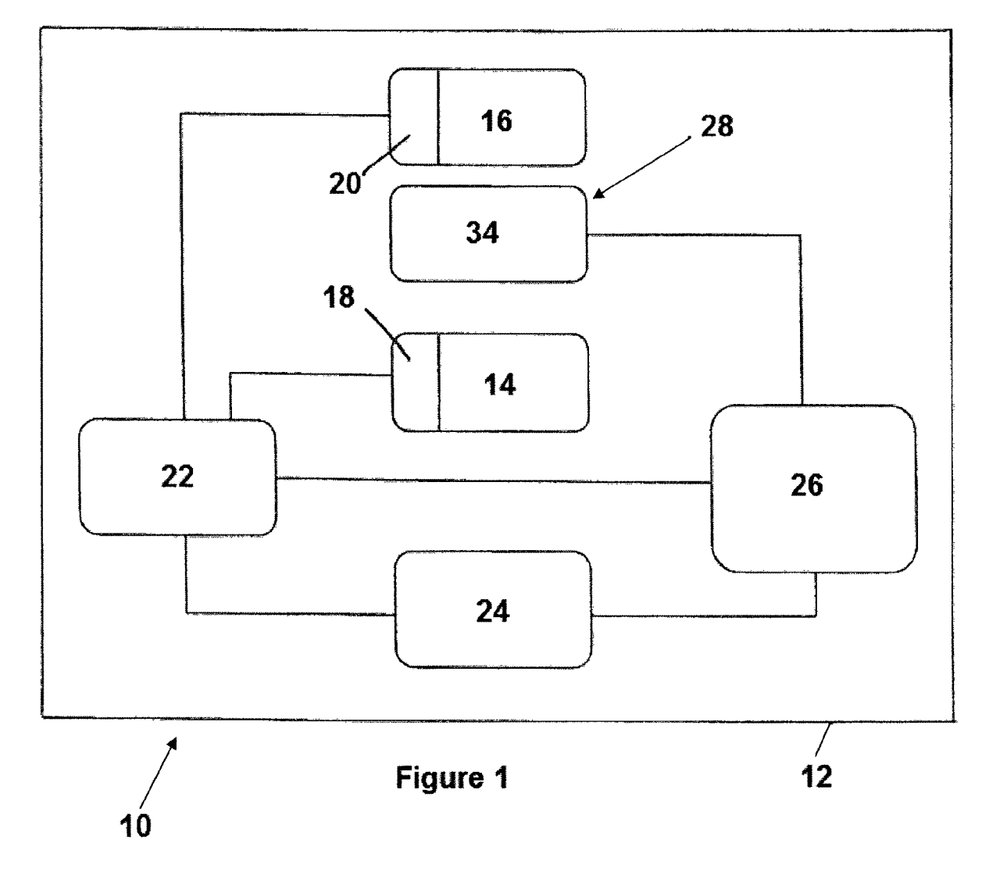
FIG. 1 is a schematic block diagram of the main components of a thermal cycler having an integrated temperature verification and calibration unit according to the invention.
Figure 2:
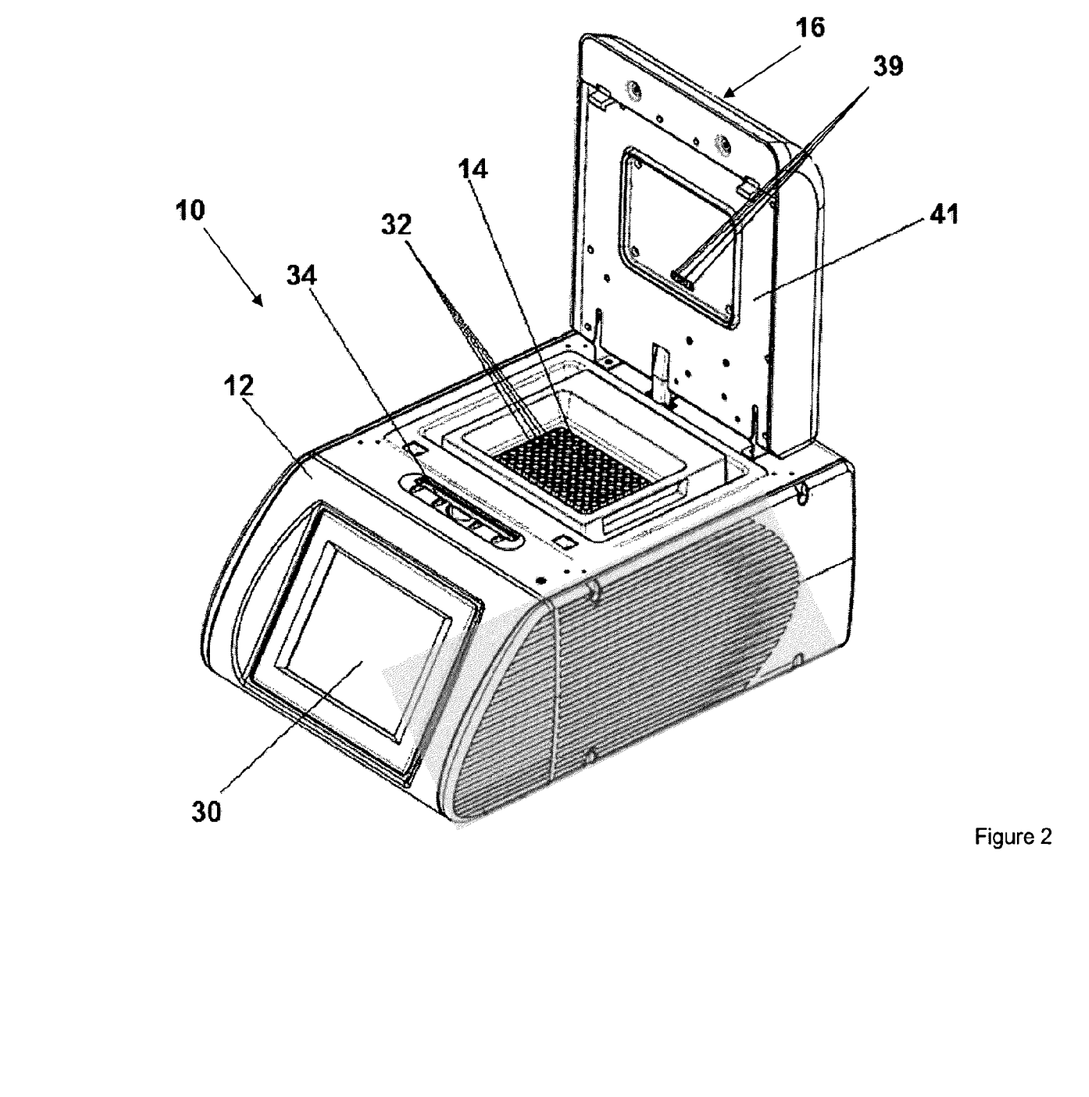
FIG. 2 is a perspective view of a preferred embodiment of a thermal cycler according to the invention with a temperature probe plate of the temperature verification and calibration unit in a stowage compartment of the thermal cycler.
Figure 3:
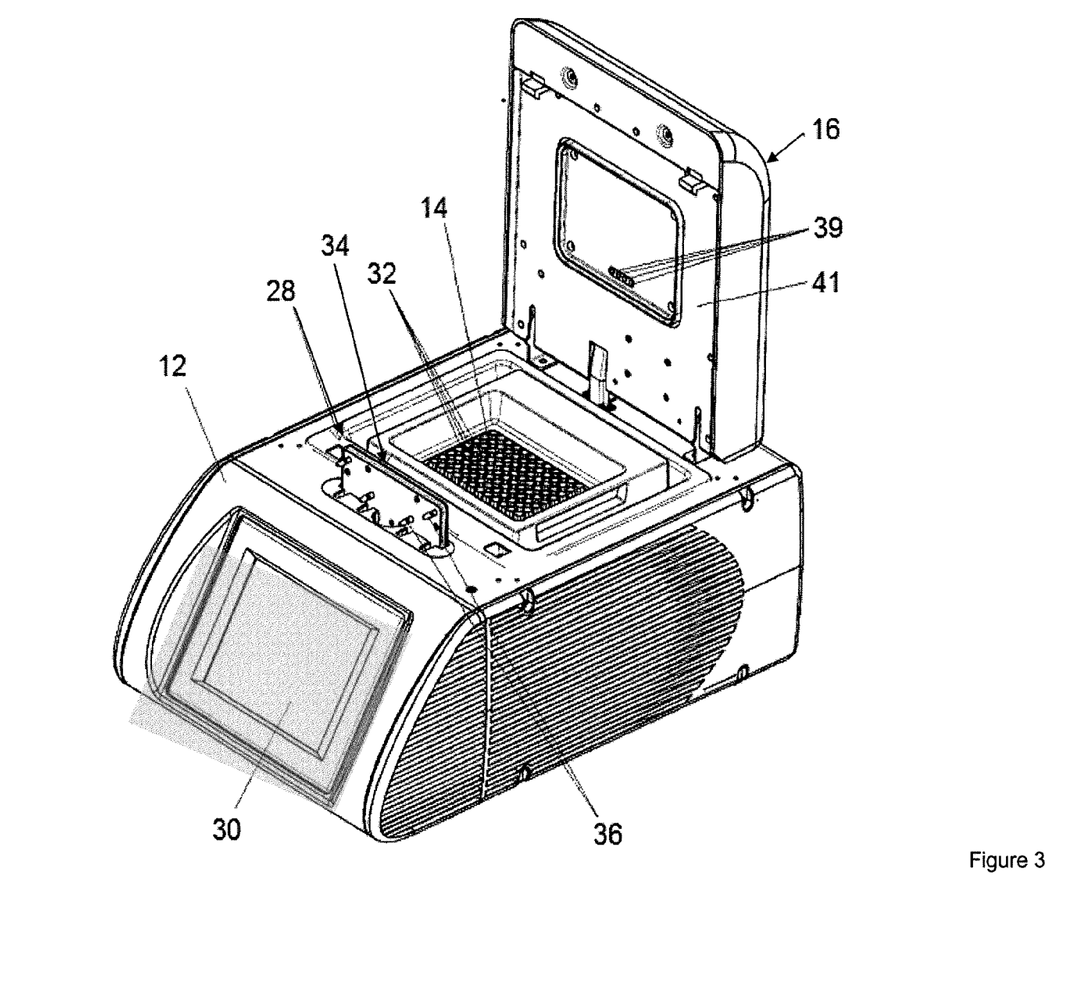
FIG. 3 is a perspective view of the embodiment during removal of the temperature probe plate from the stowage compartment.
Figures 4, 4A:
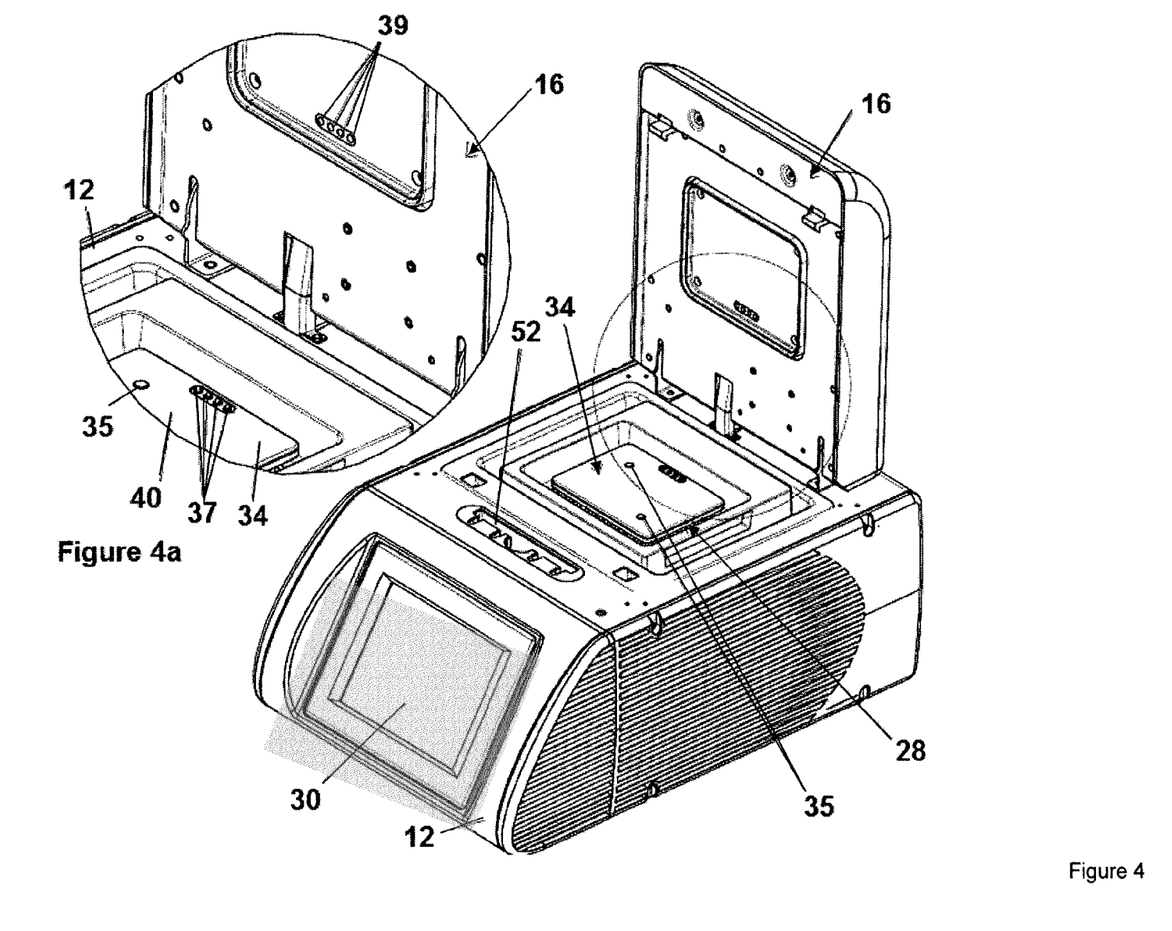
FIG. 4 is a perspective view of the embodiment with the temperature probe plate in its position of use.
FIG. 4a is a detailed view of a portion of FIG. 4.

The thermal cycler 10 depicted in the drawings is used to amplify segments of DNA via the polymerase chain reaction (PCR). As schematically shown in FIG. 1 the thermal cycler 10 comprises a housing 12 that accommodates a thermal block 14, a pivotable heated lid 16, each comprising an electric heater 18, 20, an electronic control 22 for controlling the electric heaters 18, 20 of the thermal block 14 and of the heated lid 16, a power supply 24, that is connected to the electric heaters 18, 20 through the electronic control 22, an internal single board computer and graphical interface 26, that is connected to the electronic control 22 and to the power supply 24 and an integrated temperature analysis and/or verification unit 28, that is connected to the interface 26. As depicted in FIGS. 2 to 4 of the drawing at a front of the housing 12 the thermal cycler 10 further comprises a display in the form of a user-friendly colour touch-screen 30 with drag and drop function that is connected to the electronic control 22, the power supply 24 and the internal interface 26. The thermal cycler further comprises a USB port (not shown) that is connected to the interface 26 and facilitates the storage of programs from a USB memory stick in a memory of the electronic control.

The thermal block 14 is provided with an array of vertical holes or sample wells 32 as can be best seen from FIGS. 2 and 3. The sample wells 32 are for receiving ninety six 0.2 ml sample or reaction tubes (not shown) or a 96-well PCR plate (not shown) that contain test samples or reaction mixtures to be tested. The thermal block 14 is removable so that other block types, e.g. with three hundred and eighty four sample wells, can be fitted, if required.

The electric heater 18 of the thermal block 14 comprises eight Peltier elements (not shown) that assure an exact concordance between the actual temperature of the thermal block 14 and a target temperature that is provided by operating software stored in the memory of the electronic control 22. The software controls the temperature of the thermal block 14 that is raised and lowered in discrete, pre-programmed steps for alternately heating and cooling the test samples in the sample wells 32 during the cycles of the PCR. The thermal block 14 is further provided with four temperature control sensors (not shown) for measuring the actual temperature of the thermal block 14. The temperature control sensors are connected with the electronic control 22.

In order to avoid any discrepancies or a temperature drift between the actual temperature measured by the temperature control sensors and the actual temperature within the sample wells 32 the temperature within specified sample wells 32 can be analyzed or verified with the help of the integrated temperature analysis and/or verification unit 28. The temperature analysis and/or verification unit 28 is used to perform a validation and a verification of the temperature performance of the thermal block 14 in a way that is totally independent from the temperature control of the thermal block 14 and other heated components of the thermal cycler, like the heated lid 16.

Figure 11:
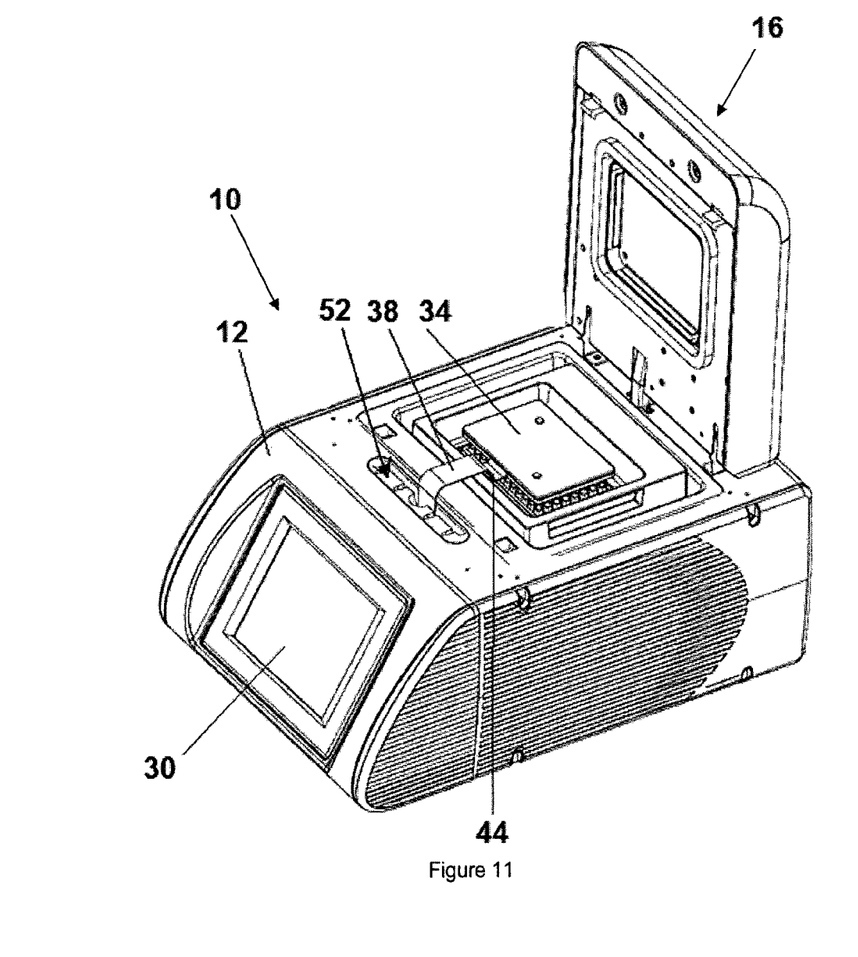
FIG. 11 is a perspective view of a second embodiment during removal of the temperature probe plate from the stowage compartment.

To this and the integrated temperature analysis and/or verification unit 28 comprises a temperature probe plate 34 having a plurality of temperature probes 36 and an embedded control electronics or computer (not shown) that may be either within the housing 12 of the thermal cycler 10 or within the temperature probe 34 plate itself. In the first instance the temperature probe plate 34 is electrically connected to the control electronics or embedded computer through the internal interface 26. In the second instance the control electronics or embedded computer within the temperature probe plate 34 is connected to the electronic control 22 and the power supply 24 through the internal interface 26, so that the temperature probe plate 34 is stand-alone, i.e. only requires powering. The electric connection can be either temporary through electrical contacts 37, 39 or a plug-in connection when the temperature probe plate 34 is located on the thermal block 14, as shown in FIGS. 2 to 4, so that the temperature probe plate 34 can be completely removed from the thermal cycler 10, e.g. for external calibration. Alternatively the electrical connection can be permanent through a cable 38, as shown in FIG. 11.

The temperature probe plate 34 has a rectangular shape with two opposite broad sides 40, 42 and four narrow sides. The dimensions of the broad sides 40, 42 essentially conform to the horizontal dimensions of the thermal block 14. The temperature probes 36 project from one 42 of the two broad sides 40, 42 of the temperature probe plate 34. The location and size of the temperature probes 36 conforms to the location and size of the sample wells 32 so that they will fit into the sample wells when the temperature probe plate 34 is placed upon the thermal block 14, as shown in FIG. 4.

Figure 7:
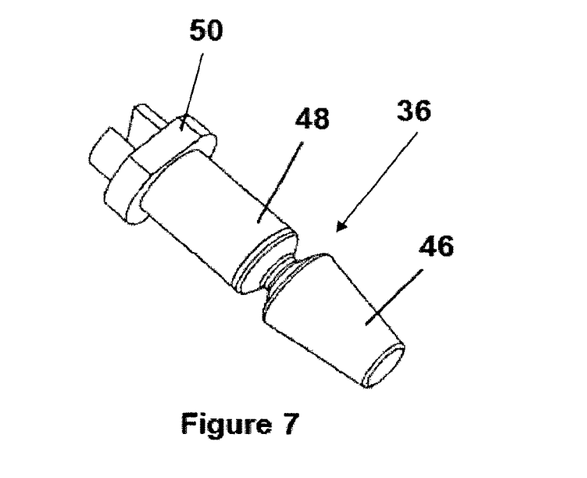
FIG. 7 is a perspective view of a temperature probe of the temperature probe plate.

The temperature probes 36 are for sensing the temperature within selected sample wells 32. As can be seen from FIG. 7, the temperature probes 36 essentially consist of a conical probe tip 46, a cylindrical probe body 48 and a plug 50 at the end of the body 48 that is opposite from the probe tip 46. The probe tip 46 is made of a thermally conductive material, shaped to match the well profile at the bottom of the samples wells 32, where the test sample or reaction mixture to be tested is located during the normal operation of the thermal cycler 10, and houses a temperature sensor (not shown) that is electrically connected through the probe body 48 and the plug 50 to a circuitry within the temperature probe plate 34. The probe body 48 is made of a thermally insulating material and designed to precisely position the probe tip 46 at the bottom of the sample well 32 without draining heat away which would effect the temperature measurement of the temperature sensor within the probe tip 46.

In the embodiments depicted in the drawing the temperature probes 36 are fixed to the temperature probe plate 34, so that they are immovable with respect to the temperature probe plate 34 and are always associated with specific sample wells 32. Preferably there are eight temperature probes 36, which are considered a suitable number of probes to give adequate coverage of the thermal block 14 in order to attain a representative measurement of its thermal uniformity.

However it can be contemplated to provide the temperature probe plate 34 with a large number of sockets (not shown) on the broad side 42, so that the plug 50 of each temperature probe 36 can be optionally attached to an arbitrary one of the sockets. In this way the temperature probes 36 are interchangeable and can be located in different sample wells 32.

If required, additional and differently shaped temperature probes 35 can be added to the opposite broad side 40 of the temperature probe plate 34 to allow for temperature measurement of the heated lid 16.

The temperature probe plate 34 is a calibrated piece of test equipment, traceable to national standards, and as such is known to be accurate. Due to the fact that the temperature probe plate 34 is completely removable from the thermal cycler 10 it can be itself calibrated or verified, independent from the thermal cycler 10.

The control electronics or embedded computer of the temperature analysis and/or verification unit 28 can comprise a separate processor and memory within the housing 12 of the thermal cycler 10 or within the temperature probe plate 34. Preferably the control electronics or embedded computer is within the temperature probe plate 34. The control electronics or embedded computer can be also part of the electronic control 22 which shares its processor and memory with the embedded computer. The embedded computer is used for performing temperature analysis or verification processes, e.g. for processing temperature measurements, and, in cooperation with the electronic control 22, self-calibration processes of the thermal cycler 10. To this end temperature analysis/verification and self-calibration software is stored within a memory of the embedded computer or within the shared memory.

In the preferred embodiment in FIGS. 2 to 4 the electrical connection between the temperature probe plate 34 and the interface 26 is by means of a plurality of electrical contact patches or protrusions 37 on the broad side 40 of the temperature probe plate 34 and a corresponding plurality of mating contact patches 39 on a lower side 41 of the heated lid 16 above the heated block 14. The contacts patches 37 and 39 respectively are disposed in the same distance from a pivot axis of the heated lid 16 so that they are pressed against each other and are in electrical contact when the temperature probe plate 34 is located on the thermal block 14 and when the heated lid 16 is pivoted on top of the broad side 40 of the temperature probe plate 34 in its closed position.

In the embodiment in FIG. 11 the electrical connection is by means of the ribbon cable 38 having a plug 44 that can be connected to a mating socket on one of the narrow sides of the temperature probe plate 34.

The function of the temperature probe plate 34 with the temperature probes 36 can be derived from FIGS. 2 to 4. In the normal operation of the thermal cycler 10 test samples or reaction mixtures are loaded into the sample wells 32 and the temperature of the thermal block 14 is raised and lowered in discrete, pre-programmed steps for alternately heating and cooling the test samples or reaction mixtures. During normal operation, e.g. during the cycles of a PCR, the temperature analysis and/or verification unit 28 is not in use and no temperature analysis and/or verification is performed. As depicted in FIG. 2, during that time the temperature probe plate 34 with the temperature probes 36 is in a stowage position within a stowage compartment 52. The stowage compartment 52 is disposed between the thermal block 14 and the display or screen 30 and is generally parallel to a back wall of the housing 12. The stowage compartment 52 has the form of a vertical slot for receiving the temperature probe plate 34 in a vertical orientation with one of the narrow sides facing downwardly. An opening 54 at the upper end of the stowage compartment 52 is flush with an upper surface of the housing 12 between the thermal block 14 and the display or screen 30.

Figure 5:
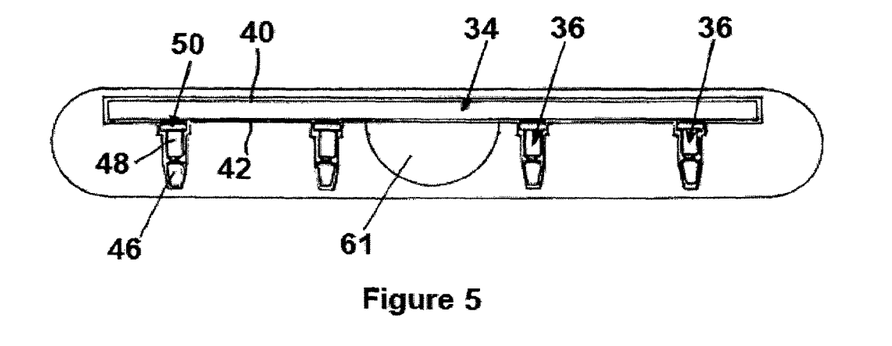
FIG. 5 is an enlarged top view of the stowage compartment during the removal of the temperature probe plate as shown in FIG. 3.
Figure 6:
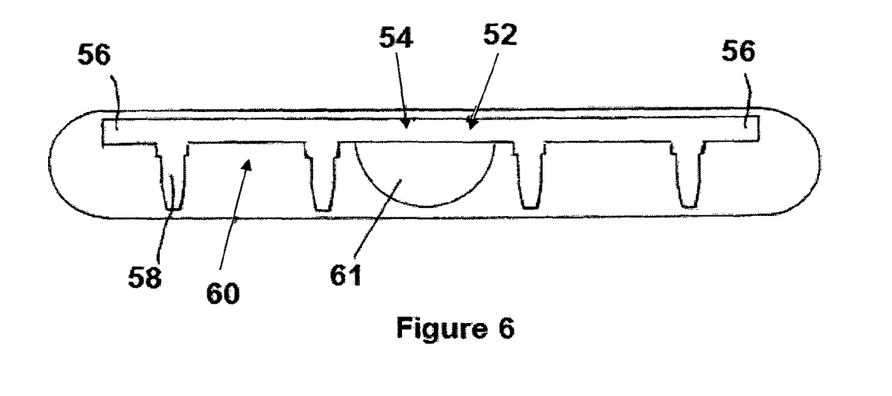
FIG. 6 is an enlarged top view of the stowage compartment without the temperature probe plate.

As can be seen best from FIGS. 5 and 6, the opening 54 of the stowage compartment 52 is provided with a guide for guiding the temperature probe plate 34 during insertion into the slot-like compartment 52 and during removal from the compartment 52. The guide comprises two vertical grooves 56 that are located at the opposite ends of the elongated opening 54 and of the compartment 52 and that receive two of the narrow sides of the temperature probe plate 34. In addition the guide comprises a number of cutouts 58 in a lid 60 that covers the stowage compartment 52 partially. The shape and location of the cutouts 58 conforms to the shape and location of the temperature probes 36 on the temperature probe plate 34 so that the temperature probes 36 will pass through the cutouts 58. The lid 60 is provided with a further cut-out 61 for facilitating the removal of the temperature probe plate 34 from the stowage position. In an embodiment where the temperature probe plate 34 is provided with interchangeable temperature probes 36 the lid 60 will be removed.

In the embodiment of FIG. 11 the ribbon cable 38 extends from the socket of the temperature probe plate 34 through the opening 54 to the bottom of the compartment 52, where it is connected to the interface 26.

When it is intended to measure the actual temperatures within the sample wells 32 in order to analyze or verify the thermal performance of the thermal cycler 10, i.e. of the thermal block 14 and the heated lid 16, the test samples or reaction mixtures are removed from the sample wells 32 and the temperature probe plate 34 is removed from the stowage compartment 52 and placed on the thermal block 14 with the temperature probes 36 within the specified sample wells 32, as shown in FIG. 4.

Figure 8:
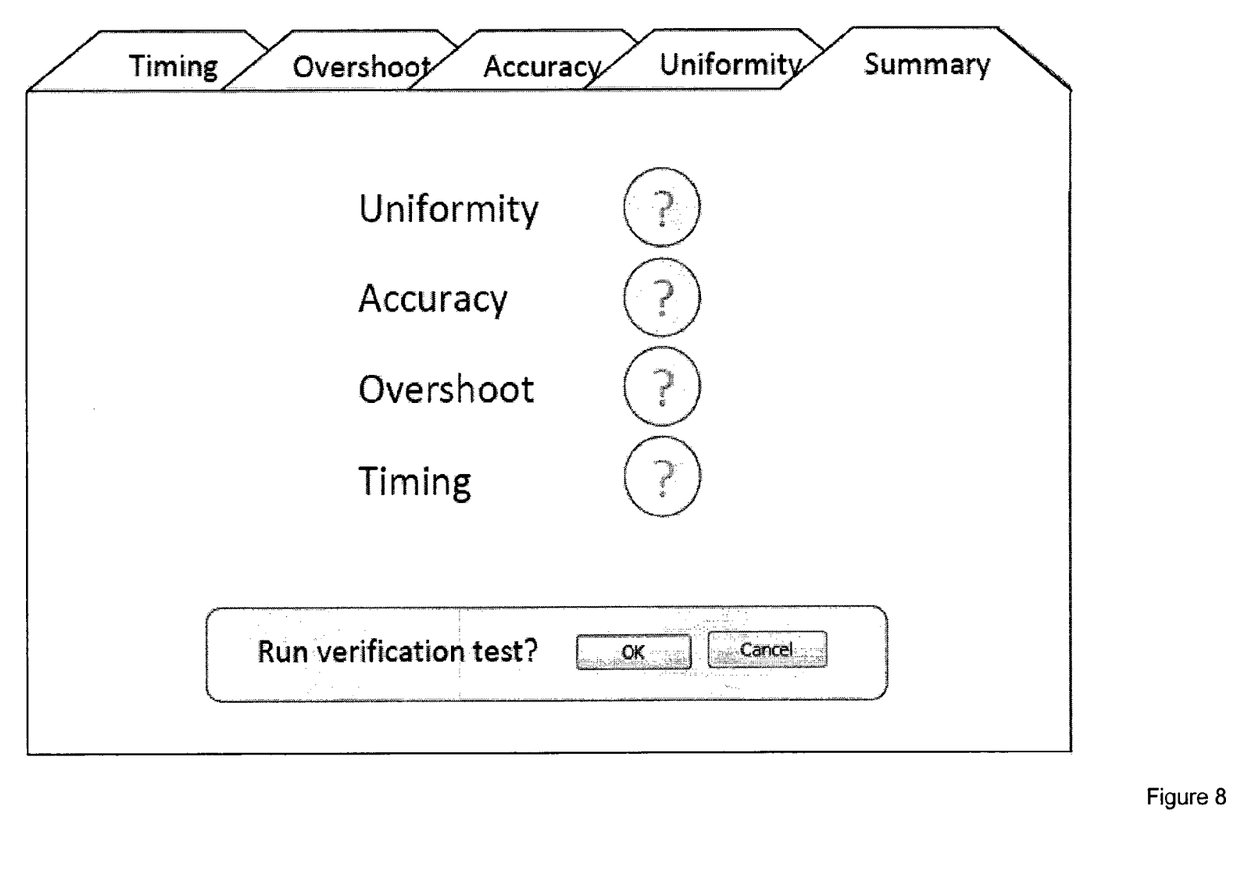
FIG. 8 is a view of a screen of the thermal cycler after the start of a temperature verification and calibration software of the thermal cycler's temperature verification and calibration unit.
Figure 9:
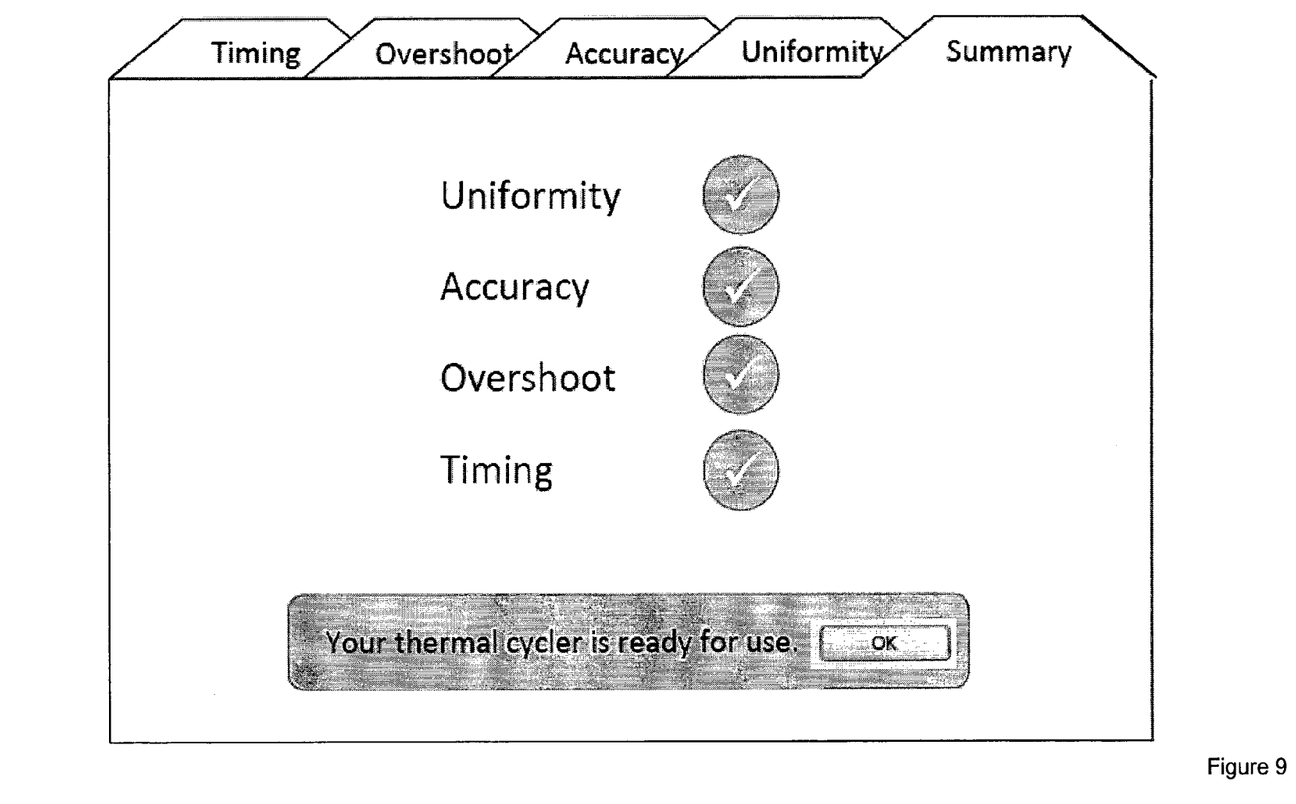
FIG. 9 is a view of the screen after the completion of a temperature verification test conducted by the thermal cycler's temperature verification and calibration unit.

After that the analysis or verification process can be started by calling an analysis/verification software routine on the touch-screen 30, as shown in FIG. 8, and by touching the ok-button. Once the test is complete the user can instantly see on the screen 30 whether the thermal uniformity of the thermal block 14, the temperature accuracy, the temperature overshoot and the timing, i.e. the thermal performance of the thermal cycler 10, are satisfactory, as shown in FIG. 9. The fact that the validation/verification of the temperature performance of the thermal block 14 performed by the temperature analysis and/or verification unit 28 is totally independent from the temperature control of the thermal block 14 and of the heated lid 16 helps to ensure that the sensors in the thermal block 14 are functioning as intended and that the thermal cycler 10 as a whole can attain published specifications. Apart from displaying the thermal performance of the thermal cycler 10 on its touch-screen 30 the thermal cycler can adjust its own performance depending upon the results of the temperature measurements taken via the temperature probe plate 34.

Figure 10:
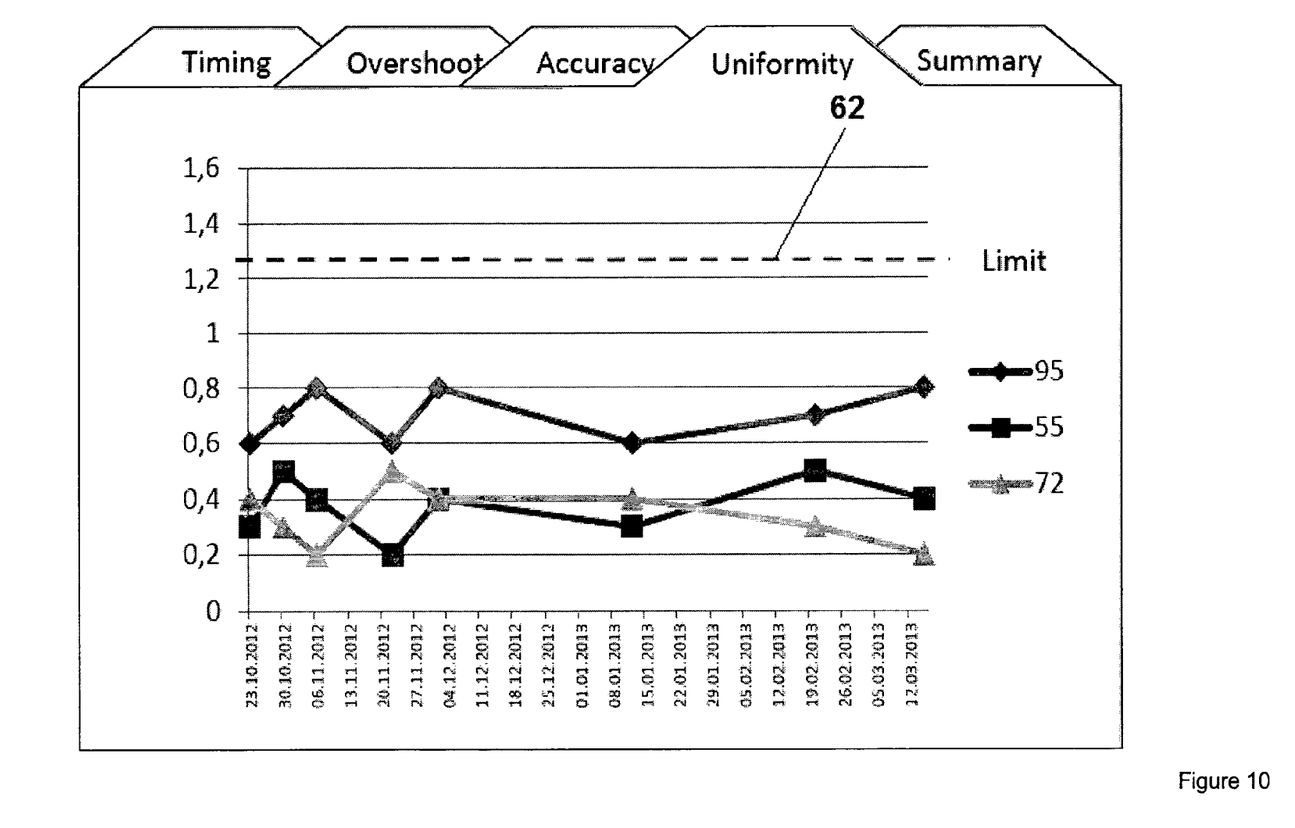
FIG. 10 is a view of the screen when displaying thermal uniformity of a thermal block of the thermal cycler against test date.

As exemplarily shown in FIG. 10 for thermal uniformity, the parameters of the thermal performance can be displayed against test time in order to visualize thermal performance history of the thermal cycler 10. As can be seen from FIG. 10, the history records displayed on the screen 30 comprise a base line or threshold barrier 62, so that the user can easily see if any of thermal uniformity, temperature accuracy, temperature overshoot and/or timing of the thermal cycler 10 exceeds the base line or threshold barrier 62 and therefore does not comply with requirements. The history records displayed on the screen can also be stored on a USB-stick via the interface 26.

In order to check that it is functioning properly the thermal cycler 10 will perform a quality control test upon demand when the temperature probe plate 34 is fitted to the thermal cycler 10. During this quality control test the thermal cycler 10 will step through a predetermined thermal or temperature program and will simultaneously interrogate the temperature probe plate 34 via the interface 26 in order to determine which temperatures are actually attained during the test. Thereafter the thermal cycler compares the actual temperature measurements against the temperatures that were set or requested by the thermal cycler 10. During this comparison any inaccuracies, i.e. differences between the actually measured temperatures and the set temperatures, can be determined.

In order to avoid that one or more of thermal uniformity, temperature accuracy, temperature overshoot and timing exceed the associated baseline or threshold barrier 62 or to avoid the inaccuracies mentioned above the thermal cycler 10 conducts a self-calibration process in regular time intervals, after each quality control test or upon demand by the user. During this self-calibration process a self-calibration software routine of the temperature analysis/verification and self-calibration software initiates a closed-loop process, where the actual or the last temperature values communicated from the temperature probes of the temperature probe plate 34 are compared with programmed target temperature values and where the temperature performance of the Peltier elements or electric heaters 18 of the thermal block 14 is modified via the electronic control 22 in dependency from the difference between the actual/last temperature values and the target temperature values.

In order to eliminate any inaccuracies furthermore the temperature probe plate 34 including all of its temperature probes 36 can be individually and externally calibrated by disconnecting the electrical contacts 37, 39 or the plug-in connection between the temperature probe plate 34 and the internal interface 26. During external calibration the temperature probes 36 of the temperature probe plate 34 are immersed in a circulated oil bath and thermally calibrated to conform to national temperature or measurement standards. Thus it becomes possible not only to validate the thermal performance of the thermal cycler 10 but also to verify it in readiness for performing a real experiment and to assure temperature measurement accuracy. With other words it is possible to make sure that a predetermined setting of the temperature with the sample wells, e.g. 95.0° C., is truly and precisely attained during the polymerase chain reaction (PCR), traceable to national standards.

The invention claimed is:

1. A method for analyzing or verifying a thermal performance of a thermal cycler (10) and for calibrating the thermal cycler (10) comprising:
   providing the thermal cycler (10) with an integrated temperature analysis and verification unit (28), the integrated temperature analysis and verification unit (28) comprising a temperature probe plate (34) having a plurality of temperature probes (36),
   measuring the temperatures within selected sample wells (32) of a thermal block (14) of the thermal cycler (10) by means of the plurality of temperature probes (36) of the temperature probe plate (34), whereby the temperature probes (36) communicate temperature values to an electronic control (22) by means of an internal interface (26) of the thermal cycler (10),
   verifying with the integrated temperature analysis and verification unit (28) that the temperatures achieved in the samples wells (32) are according to specification,
   self-calibrating the thermal cycler (10) with the integrated temperature analysis and verification unit (28),
   disconnecting an electrical connection between the temperature probe plate (34) and the thermal cycler (10), and
   removing the temperature probe plate (34) from the thermal cycler (10) for separate external calibration of the temperature probe plate (34).

2. The method according to claim 1, wherein the step of initiating a self-calibration of the thermal cycler is a closed-loop process using the temperature values communicated by the temperature probes.

3. The method according to claim 1, wherein the temperature analysis and verification unit (28) comprises a closed loop control for calibration of the electric heater means (18) using the temperature values measured by the temperature probes within selected sample wells (32).

4. A method of amplifying segments of DNA via the polymerase chain reaction comprising:
   providing a thermal cycler (10) comprising
      a housing (12), the housing (12) accommodating a thermal block (14) having a plurality of sample wells (32), each for receiving a test sample in a sample vessel,
      an electric heater means (18) for heating the thermal block (14),
      a power supply (24),
      an electronic control (22) for controlling the electric heater means (18),
      a temperature analysis and verification unit (28) for analyzing and verifying a thermal performance of the thermal block (14), the temperature analysis and verification unit (28) comprising a temperature probe plate (34) having a plurality of temperature probes (36) for measuring the temperature within selected sample wells (32), wherein the temperature analysis and verification unit (28) is integrated into the housing (14) and is connected to the power supply (24)

and to the electronic control (22) by means of an internal interface (26) and an electric connection between the temperature probe plate (34) and the interface (26) can be disconnected for removal of the temperature probe plate (34) from the thermal cycler (10) for external calibration;

placing sample vessels containing test samples or reaction mixtures in said sample wells (32) of the thermal block (14), and alternately heating and cooling the test samples in said sample vessels (32) with the thermal block (14) to amplify the segments of DNA.

\* \* \* \* \*

UNITED STATES PATENT AND TRADEMARK OFFICE
CERTIFICATE OF CORRECTION

PATENT NO. : 10,307,762 B2  
APPLICATION NO. : 15/103543  
DATED : June 4, 2019  
INVENTOR(S) : James Courtney Page 1 of 1

It is certified that error appears in the above-identified patent and that said Letters Patent is hereby corrected as shown below:

On the Title Page

Item (73), "...Hahn Lifescience GmbH..." should read --...Hain Lifescience GmbH...--

Signed and Sealed this  
Twentieth Day of October, 2020

Andrei Iancu  
*Director of the United States Patent and Trademark Office*